(12) United States Patent
Finkelstein

(10) Patent No.: US 7,202,229 B1
(45) Date of Patent: *Apr. 10, 2007

(54) ASPIRIN FORMULATION FOR CARDIOVASCULAR HEALTH

(75) Inventor: David Finkelstein, Boca Raton, FL (US)

(73) Assignee: Alan James Group, LLC., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/323,093

(22) Filed: Dec. 30, 2005

(51) Int. Cl.
| A61K 31/70 | (2006.01) |
| A61K 31/60 | (2006.01) |
| A61K 31/495 | (2006.01) |
| A61K 31/44 | (2006.01) |
| A61K 31/195 | (2006.01) |

(52) U.S. Cl. .................. 514/52; 514/161; 514/249; 514/345; 514/565; 424/754

(58) Field of Classification Search .................. None
See application file for complete search history.

(56) References Cited

U.S. PATENT DOCUMENTS

| 5,770,215 A | 6/1998 | Moshyedi ............... 424/440 |
| 5,948,443 A | 9/1999 | Riley et al. ............. 424/643 |
| 6,369,059 B1* | 4/2002 | Daugan .................. 514/250 |
| 6,914,073 B2 | 7/2005 | Boulos et al. ........... 514/458 |
| 6,953,593 B2 | 10/2005 | Kuhrts .................. 424/490 |
| 2002/0172721 A1* | 11/2002 | Boulos et al. ........... 424/646 |
| 2003/0054978 A1 | 3/2003 | Babish .................... 514/2 |
| 2003/0068365 A1 | 4/2003 | Suvanprakorn et al. .... 424/450 |
| 2004/0157932 A1* | 8/2004 | Saebo ..................... 514/625 |
| 2004/0224012 A1 | 11/2004 | Suvanprakorn et al. .... 424/450 |
| 2005/0147675 A1* | 7/2005 | Petrus .................... 424/464 |
| 2005/0233944 A1 | 10/2005 | Babish .................... 514/2 |
| 2005/0260262 A1* | 11/2005 | Dansereau et al. ........ 424/464 |
| 2006/0153823 A1 | 7/2006 | Glardeno et al. ......... 424/94.1 |

FOREIGN PATENT DOCUMENTS

| WO | WO 98/41195 | 9/1998 |
| WO | WO 03/020260 | 3/2003 |
| WO | WO 03/030818 | 4/2003 |

OTHER PUBLICATIONS

Handbook of Pharmaceutical Excipients, published by American Pharmaceutical Association (1986), pp. 138-140, 296, 297, 349 and 350.*
Gorelick & Weisman, "Risk of Hemorrhagic Stroke With Aspirin Use", Stroke. Aug. 2005;36(8):1801-7. Epub Jul. 14, 2005.
Mahe et al., "Aspirin for the Prevention of Cardiovascular Events in the Elderly", Drugs Aging. 2003;20(13):999-1010.
Newton et al., "Review article: the ageing bowel and intolerance to aspirin", Aliment Pharmacol Ther. Jan. 1, 2004;19(1):39-45.
Osiecki, "The Role of Chronic Inflammation in Cardiovascular Disease and its Regulation by Nutrients", Altern Med Rev. Mar. 2004;9(1):32-53.
Sibilia et al., "Les complications digestives et hemorragiques de l'aspirine a faible dose" Presse Med. Nov. 22, 2003;32(37 Pt 2):S17-28.

* cited by examiner

*Primary Examiner*—Raymond J. Henley, III
(74) *Attorney, Agent, or Firm*—Frommer Lawrence & Haug LLP

(57) ABSTRACT

The invention relates generally to an aspirin formulation which may comprise additional vitamins, minerals, herbs and supplements and methods for using the same for maintaining cardiovascular health. The aspirin formulation may comprise supplements such as vitamin B6, vitamin B12, folic acid, arginine and garlic. The invention also encompasses methods for maintaining healthy blood pressure and cholesterol levels with the aspirin formulation described herein.

4 Claims, No Drawings

ASPIRIN FORMULATION FOR CARDIOVASCULAR HEALTH

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Reference is also made to copending application Ser. No. 11/323,091 filed Dec. 30, 2005.

FIELD OF THE INVENTION

The invention relates generally to an aspirin formulation which may comprise additional vitamins, minerals, herbs and supplements and methods for using the same for maintaining cardiovascular health.

BACKGROUND OF THE INVENTION

Cardiovascular disease is the leading cause of death in the United States and many other countries. Nutritional factors are widely recognized as playing a role in preventing, delaying the onset of and/or slowing the progression of arteriosclerosis and coronary heart disease.

Most risk markers for cardiovascular disease have a pro-inflammatory component, which stimulates the release of a number of active molecules such as inflammatory mediators, reactive oxygen species, nitric oxide, and peroxynitrite from endothelial, vascular smooth muscle, and immune cells in response to injury (reviewed by Osiecki, Altern Med Rev. 2004 March; 9(1):32–53). Nutrients such as arginine, antioxidants (vitamins C and E, lipoic acid, glutathione), and enzyme cofactors (vitamins B2 and B3, folate, and tetrahydrobiopterin) help to elevate nitric oxide levels and may play an important role in the management of cardiovascular disease. Other dietary components such as DHA/EPA from fish oil, tocotrienols, vitamins B6 and B12, and quercetin contribute further to mitigating the inflammatory process.

Aspirin has a role in the prevention of cardiovascular and cerebrovascular disease, Alzheimer's dementia and several cancers. Encouraging all 50 year olds to take low-dose aspirin doubles their chances of living a healthy life into their nineties. The widespread use of aspirin, however, is limited as many older subjects are currently unable to take aspirin because of gastrointestinal side-effects. A review by Newton et al. (Aliment Pharmacol Ther. 2004 Jan. 1; 19(1): 39–45) explores why gastrointestinal events occur with aspirin use and how a net benefit from prophylactic aspirin might be achieved in older subjects. It is suggested that, by understanding the age-related changes in upper gastrointestinal physiology and the mechanisms by which aspirin leads to the risk reductions associated with its use, it may be possible to direct interventions to improve tolerability in older subjects.

Aspirin (acetylsalicylic acid), the most widely used antiplatelet drug, is clinically effective for the prevention of vascular ischaemic events (reviewed by Mahe et al. Drugs Aging, 2003; 20(13):999–1010). Very few primary or secondary prevention trials address the benefit-risk ratio of aspirin in the elderly. In secondary prevention, it is generally accepted that the beneficial effect of aspirin in the general patient population, demonstrated by randomised controlled trials, can be extrapolated to the elderly. Elderly patients are at relatively high risk for the development of vascular disease and might also be expected to derive substantial benefit from regular aspirin administration. Retrospective studies in the elderly found that the benefit provided by aspirin in older patients was similar or increased compared with younger individuals. In primary prevention, the potential benefit of antiplatelet agents must be balanced against the risk of bleeding, which is higher in older patients.

The gastro-intestinal (GI) toxicity associated with high dose aspirin has been fully demonstrated, but remains poorly elucidated at low doses i.e., less than 500 mg/day (reviewed by Sibilia et al., Presse Med. 2003 Nov. 22; 32(37 Pt 2):S17–28). Such toxicity is relatively difficult to study because lesional and/or bleeding GI complications are not always well described in studies. The GI risk exists, starting with the lowest doses and appears to be dose-dependent. The lesional complications consist mainly of erosive lesions, most often gastric, and rarely true ulcers. Cases of bleeding appear more frequent, but generally are minor.

Low-dose aspirin is an important therapeutic option in the prevention of cardiovascular disease, including myocardial infarction and ischemic stroke, especially in light of its unique cost-effectiveness and widespread availability (reviewed by Gorelick & Weisman, Stroke. 2005 August; 36(8):1801–7. Epub 2005 Jul. 14). In the secondary prevention of cardiovascular, cerebrovascular, and ischemic events, the evidence supports that the benefits of aspirin treatment significantly outweigh the risk of a major hemorrhage.

Attempts have been made to design multivitamin supplements specifically for heart health. Examples include U.S. Pat. No. 5,770,215, which relates to a multivitamin composition containing various vitamins, minerals, and acetylsalicylic acid, U.S. Pat. No. 5,948,443, which pertains to an acetylsalicylic acid and micronutrient supplement, U.S. Pat. No. 6,914,073 which relates to a composition containing a high level of Vitamin B in encapsulated form, U.S. Pat. No. 6,953,593, which pertains to a microencapsulation process or a sustained release formulation for oral delivery with a microencapsulated core material, International Patent Publication WO 98/41195, which encompasses a nutritional supplement containing at least one flavonoid and folic acid or folate, International Patent Publication WO 03/030818 and related U.S. patent application Ser. Nos. 10/264,205 and 10/864,149, which pertain to active agent compositions using liposome beads and International Patent Publication No. WO 03/020260 and related U.S. patent application Ser. Nos. 11/141,085 and 10/234,002, which pertain to compositions comprising at least one arginine compound or conjugate thereof and at least one member selected from the group consisting of high molecular weight aliphatic alcohol and methyl donor cofactor and conjugates thereof and methods of using the same.

There is a need for formulations with a low dose of aspirin with supplements to limit gastrointestinal toxicity to prevent cardiovascular disease.

Citation or identification of any document in this application is not an admission that such document is available as prior art to the present invention.

SUMMARY OF THE INVENTION

The invention is based, in part, on the Applicants' discovery that a combination of low dose aspirin and dietary supplements that may control cholesterol or blood pressure levels.

The invention is based upon a formulation which may comprise, consist essentially of or consist of aspirin, vitamin B6, vitamin B12, folic acid, arginine and garlic. Advantageously, the aspirin is a low dose of aspirin. The folic acid may also encompass folate. In another advantageous embodiment, the arginine may be L-arginine, the garlic may be a garlic extract, advantageously an aged garlic extract or an aged garlic extract powder. In a particularly advantageous embodiment, the formulation may comprise, consist essentially of or consist of a low dose of aspirin, vitamin B6, vitamin B12, folic acid or folate, L-arginine, aged garlic extract powder, or any combination thereof.

The invention also provides for a caplet or tablet which may comprise a formulation which may comprise, consist essentially of or consist of aspirin, vitamin B6, vitamin B12, folic acid, arginine and garlic. Advantageously, the aspirin is a low dose of aspirin. The folic acid may also encompass folate. In another advantageous embodiment, the arginine may be L-arginine, the garlic may be a garlic extract, advantageously an aged garlic extract or an aged garlic extract powder. In a particularly advantageous embodiment, the caplet or tablet comprises a formulation may comprise, consist essentially of or consist of a low dose of aspirin, vitamin B6, vitamin B12, folic acid or folate, L-arginine, aged garlic extract powder, or any combination thereof.

Advantageously, dosage per caplet or tablet of aspirin is 81 mg, vitamin B6 is 25 mg, vitamin B12 is 200 mcg, folic acid or folate is 600 mcg, arginine, advantageously L-arginine, is 200 mg and garlic, advantageously a garlic extract, an aged garlic extract or an aged garlic extract powder, is 500 mg. The caplet or tablet of may further comprise cellulose, silica and magnesium stearate. In another embodiment, the caplet or tablet may further comprise calcium carbonate, carnauba wax, colloidal silicon dioxide, crospovidone, hypromellose, lactose, magnesium stearate, maltodextrin, microcrystalline cellulose, pregelatinized starch, sodium starch glycolate, stearic acid, titanium dioxide, tracetin, zinc stearate or any combination thereof. Preferably, the caplet or tablet does not contain gluten, preservatives, sugar, sodium, milk, yeast, artificial colors, artificial flavors or any combination thereof.

Advantageously, the caplet or tablet may be enteric coated.

The present invention also provides for method of maintaining healthy blood pressure and cholesterol levels which may comprise administering any of the above-described caplets or tablets which may comprise any one of the above-described formulations to a patient in need of maintenance of healthy blood pressure and cholesterol levels. In an advantageous embodiment, the caplet or tablet may be administered once per day.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The invention is based, in part, on the Applicants' discovery that a combination of low dose aspirin and dietary supplements that may control cholesterol or blood pressure levels.

The invention is based upon a formulation which may comprise, consist essentially of or consist of aspirin, vitamin B6, vitamin B12, folic acid, arginine and garlic.

Aspirin includes, but is not limited to, all forms of acetylsalicylic acid including buffered aspirin, enteric coated aspirin, aspirin salts such as calcium acetylsalicylate, and mixtures of aspirin with acid acceptors any of which may be used in the formulation of the present invention. Advantageously, the aspirin is a low dose of aspirin. Nonsteroidal anti-inflammatory drugs (NSAIDs) are widely used for their anti-inflammatory, analgesic, and anti-pyretic effects, whereas low-dose aspirin (also an NSAID) is used for cardiovascular prophylaxis (reviewed by Laine, Rev Gastroenterol Disord. 2004; 4 Suppl 4:S33–41). The main concern limiting use of these drugs is their gastrointestinal (GI) toxicity. GI side effects include ulcers (found at endoscopy in 15%–30% of patients using NSAIDs regularly), complications such as upper GI bleeding (annual incidence of 1.0%–1.5%), and development of upper GI symptoms such as dyspepsia (occurring in up to 60% of patients taking NSAIDs).

The aspirin formulations as described in U.S. Pat. Nos. 6,967,212; 6,960,357; 6,953,593; 6,881,860; 6,852,878; 6,825,208; 6,716,869; 6,677,356; 6,673,831; 6,669,955; 6,656,482; 6,589,556; 6,585,995; 6,576,256; 6,566,384; 6,559,133; 6,492,401; 6,491,949; 6,489,341; 6,482,811; 6,407,135; 6,403,571; 6,399,079; 6,376,242; 6,310,088; 6,309,669; 6,274,170; 6,251,852; 6,245,811; 6,235,311; 6,187,924; 6,159,993; 6,102,254; 6,071,523; 6,040,147; 5,989,578; 5,916,910; 5,881,926; 5,871,766; 5,846,959; 5,846,566; 5,811,547; 5,733,572; 5,700,410; 5,292,512; 5,023,085; 4,885,287; 4,795,641; 4,559,329; 4,327,725 and 4,256,108, the disclosures of which are incorporated by reference in their entireties, may be used in the present invention.

The term "low dose aspirin" is widely known to one of skill in the art. Low dose aspirin may generally refer to a daily aspirin dose less than about 200 mg, less than about 175 mg, less than about 150 mg, less than about 125 mg and more advantageously, less than about 100 mg per day. Advantageously, a low dose of aspirin is about 90 mg, about 85 mg, about 84 mg, about 83 mg, about 82 mg and most advantageously about 81 mg.

B-vitamins, i.e. folate, vitamin B12, vitamin B6 and riboflavin, may be used in the formulations of the present invention. These B-vitamins are involved in homocysteine metabolism (reviewed by Strain et al., Proc Nutr Soc. 2004 November; 63(4):597–603). Homocysteine is a S-containing amino acid and its plasma concentrations can be raised by various constitutive, genetic and lifestyle factors, by inadequate nutrient status and as a result of systemic disease and various drugs. Hyperhomocysteinaemia is a modest independent predictor of cardiovascular disease and stroke, but causality and the precise pathophysiological mechanism(s) of homocysteine action remain unproven. The predominant nutritional cause of raised plasma homocysteine in most healthy populations is folate insufficiency. Vitamin B12 and, to a lesser extent, vitamin B6 are also effective at lowering plasma homocysteine, especially after homocysteine lowering by folic acid in those individuals presenting with raised plasma homocysteine. However, riboflavin supplementation appears to be effective at lowering plasma homocysteine only in those individuals homozygous for the T allele of the C677T polymorphism of the methylenetetrahydrofolate reductase (MTHFR) gene. This gene codes for the MTHFR enzyme that produces methyltetrahydrofolate, which, in turn, is a substrate for the remethylation of homocysteine by the vitamin B12-dependent enzyme methionine synthase. Individuals with the MTHFR 677TT genotype are genetically predisposed to elevated plasma homocysteine, and in most populations have a markedly higher risk of cardiovascular disease.

The nutritional status and plasma concentrations of some group B vitamins, namely vitamin B6, vitamin B12 and folic acid, have recently emerged as inverse correlates of cardiovascular risk, and several experimental and clinical studies, these latter mostly retrospective and case-control studies, indicate a defect of such vitamins as capable of promoting the progression of atherosclerosis (reviewed by Granieri et al., Ital Heart J Suppl. 2005 January; 6(1):1–16). Since all these vitamins are implicated in homocysteine metabolism, and since homocysteine has a well-recognized relationship with cardiovascular risk, the simplest hypothesis to explain the relationship of vitamin B6, vitamin B12 and folic acid on the one hand, and cardiovascular risk on the other is that this relationship is mediated by plasma levels of homocysteine. The most convincing literature data for the existence of a relationship with cardiovascular risk are for vitamin B6 and folic acid. These vitamins, however, have also a series of in vitro effects indicating a direct antiatherogenic action, and the results of several clinical studies, especially for vitamin B6, indicate an inverse relationship with cardiovascular risk at least in part independent of homocysteinemia. A further confirmation of these data is important to devise future intervention strategies in primary and secondary prophylaxis of atherosclerotic vascular disease.

Vitamin B6 encompasses pyridoxine hydrochloride in all physiologically acceptable forms which may be used in the formulation of the present invention. The vitamin B6 formulations as described in U.S. Pat. Nos. 6,953,588; 6,933,291; 6,921,754; 6,845,777; 6,814,983; 6,770,663; 6,770,307; 6,669,955; 6,579,899; 6,565,891; 6,551,627; 6,548,483; 6,514,544; 6,441,038; 6,420,342; 6,407,141; 6,369,041; 6,361,800; 6,338,862; 6,323,188; 6,322,504; 6,299,896; 6,291,533; 6,274,170; 6,197,309; 6,133,318; 6,133,317; 6,121,249; 6,048,846; 5,993,866; 5,985,339; 5,977,073; 5,976,568; 5,972,382; 5,948,443; 5,925,377; 5,922,704; 5,885,976; 5,397,786; 5,332,579; 5,308,627 and 5,084,482, the disclosures of which are incorporated by reference in their entireties, may be used in the present invention. Brands of vitamin B6 which may be used in the formulation of the present invention include, but are not limited to, American Health Care, Basic Drugs, Bronson, Country Life, Energen, Golden Sun, Goldline, Health For Life, Hudson, Mason, Myers, Nat Rul Health, Natural Wealth, Nature Made, Natures Blend, Nature's Bounty, Natures Life, Natures Naturals, Natures Way, Natures Wonder (Nwndr), Now, Nutri Plus, Optimum, Pharma Pure, Private Label, Radiance, Rexall, Rexall Premium, Rugby, Schiff, Sentinel, Solaray, Solgar, Sundown, Super Drugs, Synergy Plus, Thompson, Tidyman, Twenty First Century, Twinlab, Ultra Herbs, Windmill, and Your Life.

Vitamin B12 encompasses cyanocobalamin in all physiologically acceptable forms which may be used in the formulation of the present invention. The vitamin B12 formulations as described in U.S. Pat. Nos. 6,953,588; 6,933,291; 6,921,754; 6,845,777; 6,814,983; 6,770,307; 6,726,647; 6,669,955; 6,596,701; 6,565,891; 6,551,629; 6,551,627; 6,548,483; 6,514,544; 6,441,038; 6,420,342; 6,361,800; 6,338,862; 6,323,188; 6,316,024; 6,299,896; 6,291,533; 6,274,170; 6,121,249; 6,056,973; 6,048,846; 5,985,339; 5,976,568; 5,972,382; 5,948,443; 5,925,377; 5,840,880; 5,834,626; 5,811,299; 5,698,232; 5,332,579; 5,308,627 and 5,084,482, the disclosures of which are incorporated by reference in their entireties, may be used in the present invention. Brands of vitamin B12 which may be used in the formulation of the present invention include, but are not limited to, American Health Care, Basic Drugs, Basic Organics, Biochem, Bricker Labs, Bronson, Centrum, Country Life, Damiana, Douglass Labs, Dowmor, Energen, Enzymatic Therapy, Fosfo, Generic, Golden Sun, Goldline, Health For Life, Health Tech, Hudson, I L X, Jarrow, Life Time, Mason, Nat Rul Health, Natural Wealth, Nature Made, Natures Blend, Nature's Bounty, Natures Life, Natures Naturals, Natures Plus, Natures Way, Natures Wonder (Nwndr), No Shot, Now, Nutri Plus, Nutrimax Plus, Optimum, Pharma Pure, Phytopharmica, Private Label, Pro Biotiks, Radiance, Rexall, Rexall Premium, Rugby, Schiff, Sentinel, Solaray, Solgar, Source Naturals, Sundown, Super Drugs, Synergy Plus, Thompson, Tidyman, Twenty First Century, Twinlab, Ultra Herbs, Windmill and Your Life.

Folic acid encompasses folate in all physiologically acceptable forms usually free folic acid which may be used in the formulation of the present invention. The folio acid or folate formulations as described in U.S. Pat. Nos. 6,974,841; 6,949,537; 6,939,860; 6,933,291; 6,930,099; 6,921,754; 6,914,073; 6,912,492; 6,911,438; 6,899,905; 6,881,752; 6,881,419; 6,866,877; 6,863,904; 6,846,501; 6,845,777; 6,835,402; 6,833,243; 6,827,954; 6,814,983; 6,794,375; 6,790,827; 6,790,462; 6,777,237; 6,776,976; 6,774,111; 6,746,678; 6,733,764; 6,726,943; 6,720,015; 6,716,462; 6,703,371; 6,693,129; 6,693,094; 6,673,831; 6,669,955; 6,660,293; 6,646,013; 6,642,277; 6,630,160; 6,624,148; 6,605,646; 6,596,701; 6,593,101; 6,583,152; 6,579,544; 6,576,666; 6,576,256; 6,569,445; 6,565,891; 6,551,629; 6,548,483; 6,544,994; 6,544,547; 6,537,976; 6,528,496; 6,528,259; 6,524,619; 6,521,247; 6,514,544; 6,511,675; 6,500,459; 6,475,518; 6,471,968; 6,441,038; 6,436,431; 6,420,342; 6,403,129; 6,376,549; 6,369,041; 6,361,800; 6,352,713; 6,338,862; 6,329,162; 6,323,189; 6,323,188; 6,322,504; 631,604; 6,316,024; 6,315,978; 6,299,925; 6,299,896; 6,297,224; 6,291,533; 6,274,170; 6,270,774; 6,267,987; 6,265,391; 6,251,857; 6,248,375; 6,245,797; 6,245,360; 6,218,120; 6,210,686; 6,207,651; 6,207,190; 6,203,818; 6,191,133; 6,190,693; 6,156,355; 6,150,168; 6,129,918; 6,127,370; 6,121,249; 6,117,872; 6,099,854; 6,086,910; 6,074,821; 6,056,973; 6,054,128; 6,051,260; 6,048,846; 6,042,849; 6,039,978; 6,033,884; 6,008,221; 5,994,109; 5,993,866; 5,985,665; 5,985,339; 5,977,073; 5,976,568; 5,976,548; 5,972,382; 5,962,062; 5,962,030; 5,962,020; 5,948,443; 5,922,704; 5,885,976; 5,849,338; 5,820,847; 5,811,547; 5,807,586; 5,795,873; 5,770,215; 744,161; 5,700,410; 5,691,325; 5,691,324; 5,688,488; 5,654,011; 5,569,477; 5,563,126; 5,538,734; 5,536,506; 5,518,730; 5,470,846; 5,416,016; 5,340,603; 5,132,113; 5,059,595; 4,557,934 and 4,058,122, the disclosures of which are incorporated by reference in their entireties, may be used in the present invention. Brands of folio acid which may be used in the formulation of the present invention include, but are not limited to, Basic Drugs, Basic Organics, Bronson, Centrum, Country Life, Cvc, Energen, Goldline, Health For Life, Landau, Mason, Mutual Drug, Natrol, Natural Wealth, Nature Made, Natures Blend, Nature's Bounty, Natures Life, Natures Naturals, Natures Plus, Natures Way, Natures Wonder (Nwndr), Now, Nutri Plus, Olay, Pharma Pure, Private Label, Radiance, Rainbow Light, Rexall, Rexall Premium, Rugby, Schiff, Sentinel, Solaray, Solgar, Source Naturals, Sundown, Superior Health Nutrition, Synergy Plus, Twenty First Century, Twinlab, Ultra Herbs, Windmill and Your Life.

In another embodiment, brands of a mixture of folic acid, vitamin B6 and vitamin B12 which may be used in the formulation of the present invention include, but are not limited to, Folgard, Mason and Sundown.

Any form of arginine may be used in the formulation of the present invention. In another advantageous embodiment, the arginine may be L-arginine. Oral treatment with L-arginine improves endothelial dysfunction in hypertensives and lowers the blood pressure (reviewed by Bolad & Delafontaine, Curr Opin Cardiol. 2005 July; 20(4):270–4). There is also increasing interest in agentia combining the property of upregulating NO-synthase (e.g. L-arginine) and restoring the balance between NO and free radicals (e.g. tetrahydrobiopterin) (reviewed by Moens et al., Int J Cardiol. 2005 Apr. 20; 100(2):179–90). One of such agents could be folic acid. Furthermore, L-arginine, the substrate for NO synthesis, and the anti-oxidants ascorbate and alpha-tocopherol, are able to increase NO synthesis and bioavailability respectively (see, e.g., Woodman, Expert Opin Pharmacother. 2001 November; 2(11):1765–75).

The arginine formulations as described in U.S. Pat. Nos. 6,953,593; 6,911,455; 6,896,899; 6,869,973; 6,825,185; 6,797,705; 6,740,327; 6,706,724; 6,693,122; 6,656,966; 6,649,629; 6,620,821; 6,617,359; 6,548,483; 6,544,994; 6,528,507; 6,524,593; 6,495,530; 6,471,997; 6,451,850; 6,444,816; 6,420,342; 6,417,207; 6,395,299; 6,369,067; 6,342,481; 6,335,023; 6,284,277; 6,255,296; 6,245,811; 6,159,485; 6,127,414; 6,054,453; 6,033,654; 6,004,933; 5,968,983; 5,906,987; 5,886,041; 5,883,128; 5,811,547; 5,795,574; 5,750,572; 5,747,514; 5,733,572; 5,702,688; 5,643,964; 5,543,430; 5,187,183; 5,073,547; 4,920,098; 4,631,283 and 4,452,735, the disclosures of which are incorporated by reference in their entireties, may be used in the present invention.

Garlic and its preparations have been widely recognized as agents for prevention and treatment of cardiovascular and other metabolic diseases, atherosclerosis, hyperlipidemia, thrombosis, hypertension and diabetes (reviewed by Banerjee & Maulik, Nutr J. 2002 Nov. 19; 1:4). Oxidative modification of DNA, proteins and lipids by reactive oxygen species (ROS) plays a role in aging and disease, including cardiovascular, neurodegenerative and inflammatory diseases and cancer (reviewed by Borek, J Nutr. 2001 March; 131(3s):1010S–5S). Extracts of fresh garlic that are aged over a prolonged period to produce aged garlic extract (AGE) contain antioxidant phytochemicals that prevent oxidant damage. These include unique water-soluble organosulfur compounds, lipid-soluble organosulfur components and flavonoids, notably allixin and selenium. Long-term extraction of garlic (up to 20 mo) ages the extract, creating antioxidant properties by modifying unstable molecules with antioxidant activity, such as allicin, and increasing stable and highly bioavailable water-soluble organosulfur compounds, such as S-allylcysteine and S-allylmercaptocysteine. AGE exerts antioxidant action by scavenging ROS, enhancing the cellular antioxidant enzymes superoxide dismutase, catalase and glutathione peroxidase, and increasing glutathione in the cells. AGE inhibits lipid peroxidation, reducing ischemic/reperfusion damage and inhibiting oxidative modification of LDL, thus protecting endothelial cells from the injury by the oxidized molecules, which contributes to atherosclerosis, AGE inhibits the activation of the oxidant-induced transcription factor, nuclear factor (NF)-kappa B, which has clinical significance in human immunodeficiency virus gene expression and atherogenesis. AGE protects DNA against free radical-mediated damage and mutations, inhibits multistep carcinogenesis and defends against ionizing radiation and UV-induced damage, including protection against some forms of UV-induced immunosuppression AGE may have a role in protecting against loss of brain function in aging and possess other antiaging effects, as suggested by its ability to increase cognitive functions, memory and longevity in a senescence-accelerated mouse model. AGE has been shown to protect against the cardiotoxic effects of doxorubicin, an antineoplastic agent used in cancer therapy and against liver toxicity caused by carbon tetrachloride (an industrial chemical) and acetaminophen, an analgesic. Substantial experimental evidence shows the ability of AGE to protect against oxidant-induced disease, acute damage from aging, radiation and chemical exposure, and long-term toxic damage. Although additional observations are warranted in humans, compelling evidence supports the beneficial health effects attributed to AGE, i.e., reducing the risk of cardiovascular disease, stroke, cancer and aging, including the oxidant-mediated brain cell damage that is implicated in Alzheimer's disease.

Any form of garlic which may be used in the formulation of the present invention. The garlic may be a garlic extract, advantageously an aged garlic extract or an aged garlic extract powder. Garlic has many other health benefits beyond cholesterol: the herb also fights cancer and greatly enhances immune system function. The garlic may be a garlic supplement, advantageously an aged garlic supplement (e.g., available from Kyolic). In a preferred embodiment, the aged garlic extract is Aged Garlic Extract™ (bulb).

The garlic formulations as described in U.S. Pat. Nos. 6,953,593; 6,949,264; 6,932,989; 6,930,099; 6,866,864; 6,858,398; 6,692,789; 6,689,588; 6,630,160; 6,620,440; 6,579,543; 6,555,134; 6,440,464; 6,423,742; 6,379,714; 6,326,031; 6,309,676; 6,197,309; 6,171,635; 6,156,355; 6,129,918; 6,048,846; 5,976,568; 5,976,549; 5,948,443; 5,883,086; 5,641,533 and 5,626,901, the disclosures of which are incorporated by reference in their entireties, may be used in the present invention.

In a particularly advantageous embodiment, the formulation may comprise, consist essentially of or consist of a low dose of aspirin, vitamin B6, vitamin B12, folic acid or folate, L-arginine, aged garlic extract powder, or any combination thereof.

The compounds of the present invention are advantageously useful in preventing or treating cardiovascular diseases, such as, but not limited to, atherosclerotic vascular disease, hypertension, heart failure, pulmonary hypertension and renal diseases. Advantageously, the compounds of the present invention provides a method for maintaining healthy blood pressure and cholesterol levels which may comprise administering any of the above-described caplets or tablets which may comprise any one of the above-described formulations to a patient in need of maintenance of healthy blood pressure and cholesterol levels. In an advantageous embodiment, the caplet or tablet may be administered once per day.

Keeping cholesterol and blood pressure levels within a healthy range helps control two of the key risk factors for heart disease. There are two main types of cholesterol in the body. One type, named HDL for high-density lipoprotein is known as the "good" cholesterol, while the other type, named LDL for low-density lipoprotein, is known as the "bad" cholesterol. LDL (the "bad" type) can cause a buildup of fatty deposits, or plaque, that can clog arteries and make the heart work harder. In contrast, HDL (the "good" type), carries LDL away from the arteries, lowering the risk of heart disease. High blood pressure can creep up on an individual and become a problem without the individual knowing it, which is why it is sometimes referred to as the "silent killer." High blood pressure can develop when arteries are narrowed, making it harder for blood to flow through them. The result places a strain on the blood vessels and is a reason why high blood pressure can lead to heart disease. Without being bound by theory, the formulation of the present invention may protect the heart by keeping blood flowing freely.

When administered to a patient, a compound of the invention is preferably administered as component of a composition that optionally comprises a pharmaceutically acceptable vehicle. The present compositions, which comprise a compound of the invention, are preferably administered orally. The compositions of the invention may also be administered by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compounds of the invention.

In certain embodiments, the present compositions may comprise one or more compounds of the invention.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound of the invention into the bloodstream.

In an advantageous embodiment, the administration is oral.

In an advantageous embodiment, the composition is enteric coated to prevent dissolution in the stomach. Advantageously, there is slow dissolution of the active substance until the tablet reaches the gastrointestinal tract. In a preferred embodiment, the compounds of the present invention are rapidly dispersed in the gastrointestinal tract.

In a less preferred embodiment, the compounds of the invention can be delivered in a vesicle, in particular a liposome (see Langer, 1990. Science 249:1527–1533; Treat et al, in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid).

In yet another less preferred embodiment, the compounds of the invention can be delivered in a controlled release system (see, e.g., Goodson, in Medical Applications of Controlled Release, supra, vol. 2, pp. 115–138 (1984)). Other controlled-release systems discussed in the review by Langer, 1990, Science 249:1527–1533) may be used. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target of a compound of the invention, thus requiring only a fraction of the systemic dose.

The present compositions can optionally comprise a suitable amount of a pharmaceutically acceptable vehicle so as to provide the form for proper administration to the patient.

In a specific embodiment, the torn "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The present compositions can take the form of solutions, suspensions, emulsion, tablet %, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro ed., Mack Publishing Co. Easton, Pa., 19th ed., 1995, pp. 1447 to 1676, incorporated herein by reference.

Advantageously, the composition is administered in the form of a caplet or a tablet. A tablet generally refers to a small solid pill containing a measured medicinal dose, usually intended to be taken orally. A caplet generally refers to a tablet of medicine taken orally. The terms tablet and caplet may be used interchangeably.

In a preferred embodiment, the compounds of the invention are formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry, coloring agents;

and preserving agents, to provide a pharmaceutically palatable preparation. Moreover, where in tablet or pill form the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A nine delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions may also include a solubilizing agent.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of a compound of the invention or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound of the invention is administered, or if a compound of the invention is administered with a therapeutic agent, then the preferred dosages correspond to the total amount administered. Oral compositions preferably contain about 10% to about 95% active ingredient by weight.

The dosage of aspirin may be less than about 500 mg, less than about 450 mg, less than about 400 mg, less than about 350 mg, less than about 300 mg, less than about 250 mg, less than about 200 mg, less than about 175 mg, less than about 150 mg, less than about 125 mg and more advantageously, less than about 100 mg per day. Advantageously, a low dose of aspirin is about 90 mg, about 85 mg, about 84 mg, about 83 mg, about 82 mg and most advantageously about 81 mg. The dosage of aspirin may also be about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg or about 10 mg.

The dosage of vitamin B6 may be about 100 mg, about 95 mg, about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 29 mg, about 28 mg, about 27 mg, about 26 mg, advantageously about 25 mg, about 24 mg, about 23 mg, about 22 mg, about 21 mg, about 20 mg, about 15 mg, about 10 mg or about 5 mg.

The dosage of vitamin B12 may be about 1000 mcg, about 950 mg, about 900 mcg, about 850 mcg, about 800 mcg, about 750 mcg, about 700 mcg, about 650 mcg, about 600 mcg, about 550 mcg, about 500 mcg, about 450 mcg, about 400 mcg, about 350 mcg, about 300 mcg, about 250 mcg, about 240 mcg, about 230 mcg, about 220 mcg, about 210 mg, advantageously about 200 mcg, about 190 mcg, about 180 mcg, about 170 mcg, about 160 mcg, about 150 mcg, about 100 mcg or about 50 mcg.

The dosage of folic acid or folate may be about 3000 mcg, mcg, about 2900 mcg, about 2800 mcg, about 2700 mcg, about 2600 mcg, about 2500 mcg, about 2400 mcg, about 2300 mcg, about 2200 mcg, about 2100 mcg, about 2000 mcg, about 1900 mcg, about 1800 mcg, about 1700 mcg, about 1600 mcg, about 1500 mcg, mcg, about 1400 mcg, about 1300 mcg, about 1200 mcg, about 1100 mcg, about 1000 mcg, about 950 mg, about 900 mcg, about 850 mcg, about 800 mcg, about 750 mcg, about 700 mcg, about 690 mcg, about 680 mcg, about 670 mcg, about 660 mcg, about 650 mcg, about 640 mcg, about 630 mcg, about 620 mcg, about 610 mcg, about advantageously about 600 mcg, about 590 mcg, about 580 mcg, about 570 mcg, about 560 mcg, about 550 mcg, about 540 mcg, about 530 mcg, about 520 mcg, about 510 mcg, about 500 mcg, about 450 mcg, about 400 mcg, about 350 mcg, about 300 mcg, about 250 mcg, about 200 mcg, about 150 mcg or about 100 mcg.

The dosage of arginine may be about 1000 mg, about 950 mg, about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 240 mg, about 230 mg, about 220 mg, about 210 mg, advantageously about 200 mg, about 190 mg, about 180 mg, about 170 mg, about 160 mg, about 150 mg, about 100 mg or about 50 mg.

The dosage of garlic may be about 3000 mg, mg, about 2900 mg, about 2800 mg, about 2700 mg, about 2600 mg, about 2500 mg, about 2400 mg, about 2300 mg, about 2200 mg, about 2100 mg, about 2000 mg, about 1900 mg, about 1800 mg, about 1700 mg, about 1600 mg, about 1500 mg, mg, about 1400 mg, about 1300 mg, about 1200 mg, about 1100 mg, about 1000 mg, about 950 mg, about 900 mg, about 850 mg, about 800 mg, about 750 mg, about 700 mg, about 600 mg, about 590 mg, about 580 mg, about 570 mg, about 560 mg, about 550 mg, about 540 mg, about 530 mg, about 520 mg, about 510 mg, advantageously about 500 mg, about 490 mg, about 480 mg, about 470 ml, about 460 mg, about 450 mg, about 440 mg, about 430 mg, about 420 mg, about 410 mg, about 400 mg, about 350 mg, about 300 mg, about 250 mg, about 200 mg, about 150 mg or about 100 mg.

Advantageously, dosage per caplet or tablet of aspirin is about 81 mg, vitamin B6 is about 25 mg, vitamin B12 is about 200 mcg, folic acid or folate is about 600 mcg, arginine, advantageously L-arginine, is about 200 mg and garlic, advantageously a garlic extract, an aged garlic extract or an aged garlic extract powder, is about 500 mg.

The caplet or tablet of may further comprise cellulose, silica and magnesium stearate. In another embodiment the caplet or tablet may further comprise calcium carbonate, carnauba wax, colloidal silicon dioxide, crospovidone, hypromellulose, lactose, magnesium stearate, maltodextrin, microcrystalline cellulose, pregelatinized starch, sodium starch glycolate, stearic acid, titanium dioxide, tracetin, zinc stearate or any combination thereof. Preferably, the caplet or tablet does not contain gluten, preservatives, sugar, sodium, milk, yeast, artificial colors, artificial flavors or any combination thereof.

The invention also provides pharmaceutical packs or kits comprising one or more vessels containing one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a therapeutic agent and a compound of the invention.

The compounds of the invention are preferably assayed in vitro and in vivo, for the desired therapeutic or prophylactic activity, prior to use in humans. For example, in vitro assays can be used to determine whether it is preferable to administer a compound of the invention alone or in combination with another compound of the invention and/or a therapeutic agent. Animal model systems can be used to demonstrate safety and efficacy.

Other methods will be known to the skilled artisan and are within the scope of the invention.

In certain embodiments of the present invention, a compound of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as or in a different composition from that comprising the compound of the invention. In another embodiment, a composition comprising a compound of the invention is administered prior or subsequent to administration of another therapeutic agent. As many of the disorders for which the compounds of the invention are useful in treating are chronic, in one embodiment combination therapy involves alternating between administering a composition comprising a compound of the invention and a composition comprising another therapeutic agent, e.g., to minimize the toxicity associated with a particular drug. The duration of administration of the compound of the invention or therapeutic agent can be, e.g., one month, three months, six months, a year, or for more extended periods. In certain embodiments, when a compound of the invention is administered concurrently with another therapeutic agent that potentially produces adverse side effects including, but not limited to, toxicity, the therapeutic agent can advantageously be administered at a dose that fans below the threshold at which the adverse side is elicited.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A formulation consisting of aspirin, vitamin B6, vitamin B12, folic acid, arginine and garlic.

2. The formulation of claim 1, wherein the aspirin is a low dose of aspirin, wherein the low dose aspirin is a daily aspirin dose less than about 200 mg.

3. The formulation of claim 1, wherein the folic acid is folate.

4. The formulation of claim 1, wherein the arginine is L-arginine.

* * * * *